(12) United States Patent
Fowler et al.

(10) Patent No.: US 10,407,357 B2
(45) Date of Patent: Sep. 10, 2019

(54) INTEGRATED PRODUCT BY PROCESS FOR POLY OLEFIN PRODUCTION WITH REDUCED GREENHOUSE GAS EMISSION

(71) Applicants: James Nicholas Fowler, Odessa, TX (US); Deborah Lawrence, Odessa, TX (US); Stephen Craig McHaney, Odessa, TX (US)

(72) Inventors: James Nicholas Fowler, Odessa, TX (US); Deborah Lawrence, Odessa, TX (US); Stephen Craig McHaney, Odessa, TX (US)

( * ) Notice: Subject to any disclaimer, the term of this patent is extended or adjusted under 35 U.S.C. 154(b) by 0 days.

(21) Appl. No.: 16/384,048

(22) Filed: Apr. 15, 2019

(65) Prior Publication Data

US 2019/0241482 A1    Aug. 8, 2019

Related U.S. Application Data

(63) Continuation-in-part of application No. 16/102,978, filed on Aug. 14, 2018, now Pat. No. 10,322,981.

(51) Int. Cl.
*C07C 11/02* (2006.01)
*C07C 2/08* (2006.01)
(Continued)

(52) U.S. Cl.
CPC ............... *C07C 2/08* (2013.01); *C07C 2/84* (2013.01); *C07C 5/2506* (2013.01); *C07C 6/04* (2013.01)

(58) Field of Classification Search
CPC ........... C07C 1/24; C07C 11/04; C07C 11/08; C07C 11/02; C07C 11/06; C07C 15/02; C07C 2/82; C07C 31/205; C07C 37/20; C07C 37/50; C07C 4/06; C07C 51/16; C07C 5/25; C07C 7/04; C07C 9/16; B01D 2251/402; B01D 2251/404; B01D 2257/302; B01D 2257/404; B01D 2257/504; B01D 2257/602; B01D 53/1425; B01D 53/1475; B01D 53/1493;
(Continued)

(56) References Cited

U.S. PATENT DOCUMENTS

| | | | |
|---|---|---|---|
| 2010/0132556 A1* | 6/2010 | Constantz | B01D 53/1425 95/234 |
| 2011/0172475 A1* | 7/2011 | Peters | C07C 1/24 585/254 |
| 2014/0208753 A1* | 7/2014 | Liu | F01K 7/40 60/652 |

* cited by examiner

*Primary Examiner* — Sharon Pregler
(74) *Attorney, Agent, or Firm* — Nolte Intellectual Property Law Group

(57) ABSTRACT

A product made by a substantially zero carbon emission process for making amorphous poly alpha olefins including, converting alkanes to olefin monomers ethylene, propylene, and 1-butene or combinations thereof using renewable electric power in an oxidative-coupling of methane plant including the steps of passing alkanes through an ethylene plant while adding oxygen, passing the first polymerization grade ethylene through a 2-butene plant, passing a first of the two 2-butene streams and one of the polymerization grade ethylene through a propylene plant, and passing a second of the two 2-butene streams through a 1-butene plant. The next step in the process for making amorphous poly alpha olefins includes polymerizing at least one of the polymerization grade alkenes which includes applying a temperature of 130 degrees Fahrenheit to 175 degrees Fahrenheit to at least one of the polymerization grade alkenes and scrubbing at least one boiler stack gases.

8 Claims, 2 Drawing Sheets

(51) Int. Cl.
*C07C 5/25* (2006.01)
*C07C 6/04* (2006.01)
*C07C 2/84* (2006.01)

(58) Field of Classification Search
CPC ........ B01D 53/62; B01D 53/77; Y02C 10/04; Y02C 10/06
See application file for complete search history.

INTEGRATED PRODUCT BY PROCESS FOR POLY OLEFIN PRODUCTION WITH REDUCED GREENHOUSE GAS EMISSION

CROSS REFERENCE TO RELATED APPLICATIONS

This Continuation in Part application claims priority to and the benefit of co-pending U.S. patent application Ser. No. 16/102,978 filed on Aug. 14, 2018, entitled "INTREGRATED PROCESS FOR POLY OLEFIN PRODUCTION WITH REDUCED GREENHOUSE GAS EMISSION" and which claims the benefit of U.S. Provisional Application No. 62/321,663, filed on Apr. 12, 2016, This reference is hereby incorporated in its entirety.

FIELD

The present embodiment generally relates to the product by process and systems for the production of olefins and olefin derivatives from alkanes. The present invention further relates to environmentally-friendly processes and systems for the production of olefins and olefin derivatives that emit substantially zero carbon dioxide into the atmosphere.

BACKGROUND

A need exists for chemical processes with reduced carbon dioxide emissions.

A further need exists for chemical processes to produce alkene monomers, used to produce various polymers, with reduced carbon dioxide emissions.

The present embodiments meet these needs.

BRIEF DESCRIPTION OF THE DRAWINGS

The detailed description will be better understood in conjunction with the accompanying drawings as follows.

Figure 1:
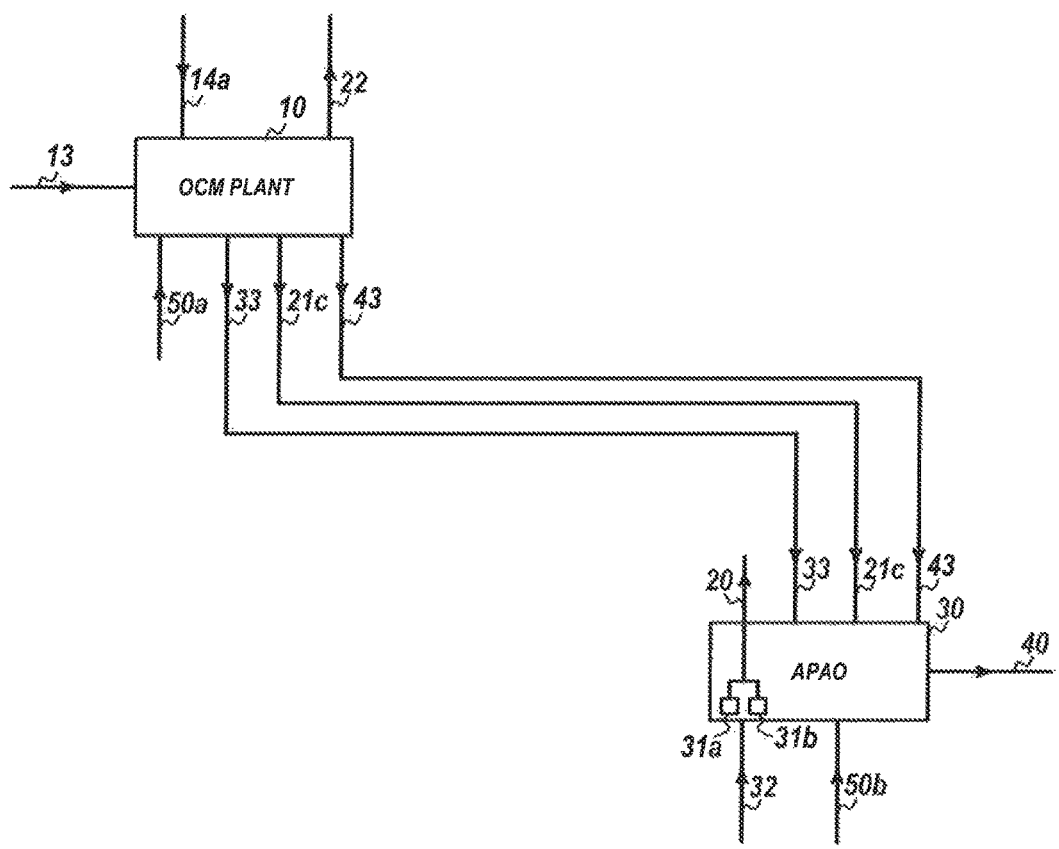
FIG. 1 depicts a substantially zero emission process according to one or more embodiments.

The present embodiments are detailed below with reference to the listed Figures.

DETAILED DESCRIPTION OF THE EMBODIMENTS

Before explaining the present process in detail, it is to be understood that the process is not limited to the particular embodiments and that it can be practiced or carried out in various ways.

Specific structural and functional details disclosed herein are not to be interpreted as limiting, but merely as a basis of the claims and as a representative basis for teaching persons having ordinary skill in the art to variously employ the present invention.

The following description of the embodiments is merely exemplary in nature and is in no way intended to limit the subject matter of the present disclosure, their application, or uses.

The present invention relates to an amorphous poly alpha olefin (APAO) made with substantially zero CO2 emissions.

The disclosed invention includes the steps of converting alkanes to ethylene, propylene, and 1-butene using renewable electric power in an oxidative-coupling of methane (OCM) plant comprising an ethylene plant, a 2-butene plant, a propylene plant, and a 1-butene plant.

The invention converts alkanes by providing an ethylene plant comprising an oxidation reactor and a first fractionation train and converting a natural gas and oxygen in the oxidation reactor to produce an oxidation reactor effluent comprising ethylene and passing the oxidation reactor effluent to the first fractionation train to recover a first ethylene stream, a second ethylene stream, and a third ethylene stream.

The invention also converts alkanes by providing a 2-butene plant comprising a dimerization unit and a second fractionation train and converting a portion of the first ethylene stream in the dimerization unit to produce a dimerization unit effluent comprising 2-butene and passing the dimerization unit effluent to the second fractionation train to recover a first 2-butene stream and a second 2-butene stream.

The invention also converts alkanes by providing a propylene plant comprising a metathesis reactor and a third fractionation train and converting a portion of the first 2-butene stream and a portion of the second ethylene stream in the metathesis reactor to produce a metathesis reactor effluent comprising propylene and passing the metathesis reactor effluent to the third fractionation train to recover the propylene.

The invention also converts alkanes by providing a 1-butene plant comprising a 2-butene isomerization unit and a fourth fractionation train and converting a portion of the second 2-butene stream in the butene isomerization unit to produce a butene isomerization unit effluent comprising 1-butene and passing the butene isomerization unit effluent to the fourth fractionation train to recover the 1-butene.

The invention discloses polymerizing any one of the 1-butene, propylene, or third ethylene stream in an APAO plant comprising boilers in which boiler stack gasses are produced.

The polymerization includes the simultaneous steps of applying a temperature of 130-175° F. to the 1-butene, the propylene or the third ethylene stream from the 1-butene plant, the propylene plant, or the ethylene plant, respectively.

The polymerization also includes scrubbing at least one of the boiler stack gasses with a solvent to sequester carbon dioxide from at least one of the boiler stack gasses.

The completion of the steps indicated above result in substantially zero CO2 emissions into the atmosphere and the formation of an amorphous poly alpha olefin.

In embodiments, the natural gas can include methane and the oxidation reactor effluent comprises unconverted methane, and can further include recycling a stream of the unconverted methane from the first fractionation train to the oxidation reactor.

In embodiments, the dimerization unit effluent can include unconverted ethylene, and further comprising recycling a stream of unconverted ethylene from the second fractionation train to the dimerization unit.

In embodiments, the metathesis reactor effluent can include unconverted ethylene and unconverted 2-butene, and further comprising recycling a stream of unconverted ethylene and unconverted 2-butene from the third fractionation train to the metathesis reactor.

In embodiments, the butene isomerization unit effluent can include unconverted 2-butene, and further comprising recycling a stream of unconverted 2-butene from the fourth fractionation train to the butene isomerization unit.

In embodiments, converting the natural gas and oxygen in the oxidation reactor to produce the oxidation reactor effluent comprising ethylene can include contacting a catalyst in the oxidation reactor with oxygen and the natural gas at a pressure from 6 bar to 16 bar and a temperature of 600 to 800° C. to produce the oxidation reactor effluent.

In embodiments, the catalyst can be selected from the group consisting of a lanthanide series metal supported catalyst and an actinide series metal supported catalyst.

The natural gas can include a mixture of alkanes and the oxidation reactor effluent can include: ethylene and carbon dioxide.

In embodiments, the dimerization unit effluent can include 2-butene and by-products.

In embodiments, the metathesis reactor effluent comprises propylene, unconverted ethylene, and unconverted 2-butene and wherein passing the metathesis reactor effluent to the third fractionation train to recover the propylene further comprises recovering the unconverted ethylene and unconverted 2-butene along with the propylene.

One of the reasons this invention is useful is that it sequesters carbon dioxide emissions during processing of monomers to make olefin derivatives.

The invention not only utilizes renewable energy sources but additionally minimizes the use of fired equipment, and for required fired equipment, scrubs the stack gases from the fired heaters with a solvent to produce a specialty polymer having a low carbon footprint.

An advantage of the process is that fewer fires can occur because only a limited number of ignition sources are used, improving safety in a plant.

An advantage of the process is that fewer explosions are expected in the chemical plant because electric heaters are not as prone to explode as gas-fired heaters.

The process reduces carbon footprint of the plant providing cleaner air.

The following terms are defined herein:

The term "1-butene plant" can refer to any of the known technologies for producing 1-butene either by chemical reaction and/or by purification of any stream containing 1-butene. In a preferred embodiment of the present invention, 1-butene can be produced by isomerization of 2-butene followed by purification.

The term "2-butene plant" can refer to any of the known technologies for producing 2-butene either by chemical reaction and/or by purification of any stream containing 2-butene. In an embodiment, 2-butene can be produced by dimerization of ethylene followed by purification.

The term "ethylene plant" can refer to any of the known technologies for producing ethylene by the oxidative coupling of methane (OCM), optionally followed by the adiabatic cracking of alkanes, and followed by the capture and sequestration of carbon dioxide from the OCM reactor effluent.

The term "amorphous poly alpha olefins" can refer to a propylene homopolymer or a polymer made from propylene and any mixture of other alpha-alkenes having no appreciable crystalline nature.

The term "olefin monomers" can refer to any alkene containing from two to twelve carbon atoms.

The term "oxidative-coupling of methane (OCM) plant" can refer to the catalytic reaction of methane in the presence of oxygen to produce alkenes.

The term "propylene plant" can refer to any of the known technologies for producing propylene by chemical reaction and/or by purification of any stream containing propylene. In embodiments, propylene can be produced by the metathesis of ethylene and butene.

The term "substantially zero $CO_2$ emission" can refer to reducing the emission of $CO_2$ to the maximum practical extent; limited only by safety and environmental regulations which require the operation of safety and emission-control devices such as flares and thermal oxidizers; and by the fact that all real separation technologies are limited by thermodynamic and chemical equilibria which never achieve a mathematically zero concentration.

As used throughout, ranges are used as shorthand for describing each and every value that is within the range. Any value within the range can be selected as the terminus of the range. Unless otherwise specified, all percentages and amounts expressed herein and elsewhere in the specification should be understood to refer to percentages by weight.

For the purposes of this specification and appended claims, unless otherwise indicated, all numbers expressing quantities, percentages or proportions, and other numerical values used in the specification and claims, are to be understood as being modified in all instances by the term "about." The use of the term "about" applies to all numeric values, whether or not explicitly indicated. This term generally refers to a range of numbers that one of ordinary skill in the art would consider as a reasonable amount of deviation to the recited numeric values (i.e., having the equivalent function or result). For example, this term can be construed as including a deviation of ±10 percent, alternatively ±5 percent, and alternatively ±1 percent of the given numeric value provided such a deviation does not alter the end function or result of the value. Accordingly, unless indicated to the contrary, the numerical parameters set forth in this specification and attached claims are approximations that can vary depending upon the desired properties sought to be obtained by the present invention.

It is noted that, as used in this specification and the appended claims, the singular forms "a," "an," and "the," include plural references unless expressly and unequivocally limited to one referent. As used herein, the term "include" and its grammatical variants are intended to be non-limiting, such that recitation of items in a list is not to the exclusion of other like items that can be substituted or added to the listed items. For example, as used in this specification and the following claims, the terms "comprise" (as well as forms, derivatives, or variations thereof, such as "comprising" and "comprises"), "include" (as well as forms, derivatives, or variations thereof, such as "including" and "includes") and "has" (as well as forms, derivatives, or variations thereof, such as "having" and "have") are inclusive (i.e., open-ended) and do not exclude additional elements or steps. Accordingly, these terms are intended to not only cover the recited element(s) or step(s), but may also include other elements or steps not expressly recited. Furthermore, as used herein, the use of the terms "a" or "an" when used in conjunction with an element may mean "one," but it is also consistent with the meaning of "one or more," "at least one," and "one or more than one." Therefore, an element preceded by "a" or "an" does not, without more constraints, preclude the existence of additional identical elements.

The present disclosure is directed to integrated processes for converting alkanes to olefins and olefins to olefin derivatives. In some instances, the alkanes are methane, ethane, propane, butane, and pentane. In other instances, the alkanes can be linear alkanes having six or more carbons. In yet other instances, the alkanes can be branched alkanes having four or more carbons. In some instances, the alkanes can be a mixture of one or more alkanes. When a mixture of one or more alkanes is used, the mixture can be delivered as a stream to a separation system or apparatus such as a fractional distillation apparatus. Separation of the individual alkanes from the mixture of one or more alkanes can take place prior to any of the integrated processes described herein or as a step during any of the integrated processes described herein. In some instances, alkanes for use in the integrated processes described herein, such as methane, can be derived from renewable biologic sources.

In some instances, the olefins produced are ethylene, propylene, and 1-butene. In other instances, the produced olefins are any olefin having four or more carbons. In some instances, the produced olefins are any olefin having a terminal alkene. Olefin derivatives produced according to various aspects of the present disclosure can be, for example, a polyalkylene such as polypropylene or polyethylene or a polyalkylene co- or terpolymer, an amorphous poly alpha olefin, an alkylene oxide such as propylene oxide or butylene oxide, a poly olefin wax, a glycol such as propylene glycol or ethylene glycol, an acrylic acid, a poly acrylic acid, or any other desired olefin derivative.

In accordance with various aspects of the present disclosure, integrated processes for converting alkanes to olefins and olefins to olefin derivatives can comprise converting alkanes to olefins and olefins to olefin derivatives at elevated temperatures, capturing carbon dioxide produced during the conversion of alkanes to olefins and olefins to olefin derivatives, and sequestering the produced carbon dioxide. The carbon dioxide can be produced as a reaction by-product or by one or more systems, apparatuses or components utilized in said integrated processes. Integrated processes according to various aspects of the present disclosure are environmentally friendly as they result in zero or substantially zero carbon emissions into the atmosphere.

Processes for converting alkanes to olefins and olefins to olefin derivatives in accordance with various aspects of the present disclosure can be conducted using renewable electric power generation for utility electric service.

In some instances, the conversion of alkanes to olefins and olefins to olefin derivatives can comprise converting alkanes to olefins and olefins to olefin derivatives at elevated temperatures using solar energy, directly or indirectly, as a heat source. In other instances, the conversion of alkanes to olefins and olefins to olefin derivatives can comprise converting alkanes to olefins and olefins to olefin derivatives at elevated temperatures using hydrocarbon fueled heaters and/or boilers as heat sources. Such heat sources can generate numerous carbon and non-carbon containing environmental pollutants such as carbon dioxide. Such environmental pollutants are generally expelled from an industrial worksite, such as a refinery or factory, in the form of flue gas. In the present disclosure, carbon dioxide in the flue gas is captured and sequestered to result in zero or substantially zero carbon emissions into the atmosphere. In some instances, an alkyl amine is used to capture produced carbon dioxide. The alkyl amine can be any one of a primary, secondary or tertiary alkyl amine. In some instances, carbon dioxide formed during the conversion of alkanes to olefins and olefins to olefin derivatives is recovered, dried, and compressed prior to sequestration.

In some instances, an oxygen-combustion technique can be used in the hydrocarbon fueled heaters and boilers to limit nitrogen based gas volumes. In other instances, an oxygen enhanced combustion technique can be used in the hydrocarbon fueled heaters and boilers to limit nitrogen based gas volumes. In yet other instances, a synthetic air (that is, a mixture of recycled flue gas and oxygen) combustion technique can be used in the hydrocarbon fueled heaters and boilers to limit nitrogen based gas volumes.

According to various aspects of the present disclosure, ethylene, produced from alkanes such as methane, are used to produce other olefins such as propylene or 1-butene. Heat inputs can be supplied with zero carbon emissions through the use of, for example, electric heaters or hydrocarbon fueled heat sources. Flue gases produced during the production of olefins from ethylene can be stripped of carbon dioxide for drying and compression prior to sequestration.

According to various aspects of the present disclosure, olefin derivatives such as polyalkylenes such as polypropylene or polyethylene or polyalkylene co- or terpolymers, amorphous poly alpha olefins, alkylene oxides such as propylene oxide or butylene oxide, poly olefin waxes, glycols such as propylene glycol or ethylene glycol, acrylic acids, poly acrylic acids, or any other desired olefin derivatives, are produced from olefins. Heat inputs can be supplied with zero carbon emissions through the use of, for example, electric heaters or hydrocarbon fueled heat sources. Flue gases produced during the production of olefins from ethylene can be stripped of carbon dioxide for drying and compression prior to sequestration.

In some instances, ethylene is produced via the oxidative coupling of methane. When olefins are produced via oxidative coupling of methane, carbon dioxide produced as a by-product during processes of the present disclosure is produced in a separate and concentrated stream and substantially zero flue gas emissions are produced.

Alkanes, olefins and olefin derivatives present in final product mixtures can be separated, by any suitable technique known to one of ordinary skill in the art, to yield pure or substantially pure alkanes, olefins, and olefin derivatives for sale or re-use in any of integrated processes according to the present disclosure. In some instances, final product mixtures are subjected to a fractional distillation process to isolate alkanes, olefins, and olefin derivatives contained therein. In instances where only olefins are produced, such fractional distillation process can be used to isolate unreacted alkanes from the olefin product.

Although the present invention and its objects, features and advantages have been described in detail, other embodiments are encompassed by the invention. Finally, those skilled in the art should appreciate that they can readily use the disclosed conception and specific embodiments as a basis for designing or modifying other structures for carrying out the same purposes of the present invention without departing from the scope of the invention as defined by the appended claims.

FIG. 1 depicts a substantially zero emission process for making amorphous poly alpha olefins according to one or more embodiments.

The substantially zero emission process can convert alkanes 14 to the olefin monomers ethylene, propylene, and butene or combinations thereof using renewable electric power 50a in an oxidative-coupling of methane (OCM) plant 10 by using the following steps:

The steps include using an ethylene plant to make ethylene from a natural gas with oxygen.

The ethylene plant to make ethylene can include fractionating in a first fractionation train 20 the mixture of monomers forming a first, second, and third polymerization grade ethylene streams 21c and a carbon dioxide stream 22.

The steps include using a 2-butene plant to convert the ethylene to create two 2-butene streams.

The steps include using a propylene plant to convert the first 2-butene stream and some of the ethylene to form propylene.

The propylene plant to convert the 2-butene and some of the ethylene to form propylene can include fractionating the propylene with unconverted ethylene and butene 31a in a third fractionation train 32 forming polymerization grade propylene 33.

The steps include using a 1-butene plant to isomerize the second 2-butene stream into 1-butene;

The substantially zero emission process can polymerize any one of the created 1-butene, propylene or ethylene in an APAO plant 30, which contains the following simultaneous steps.

The steps can include applying a temperature of 130 degrees to 175 degrees Fahrenheit to the 1-butene, propylene or ethylene from the olefins plant.

While using renewable electric power 50b and scrubbing at least one boiler stack gasses 31a and 31b, with a solvent 32 to sequester carbon dioxide 20 from the boiler stack gas.

The two step process results in substantially zero carbon emissions into the atmosphere to create amorphous poly alpha olefin.

Figure 2:
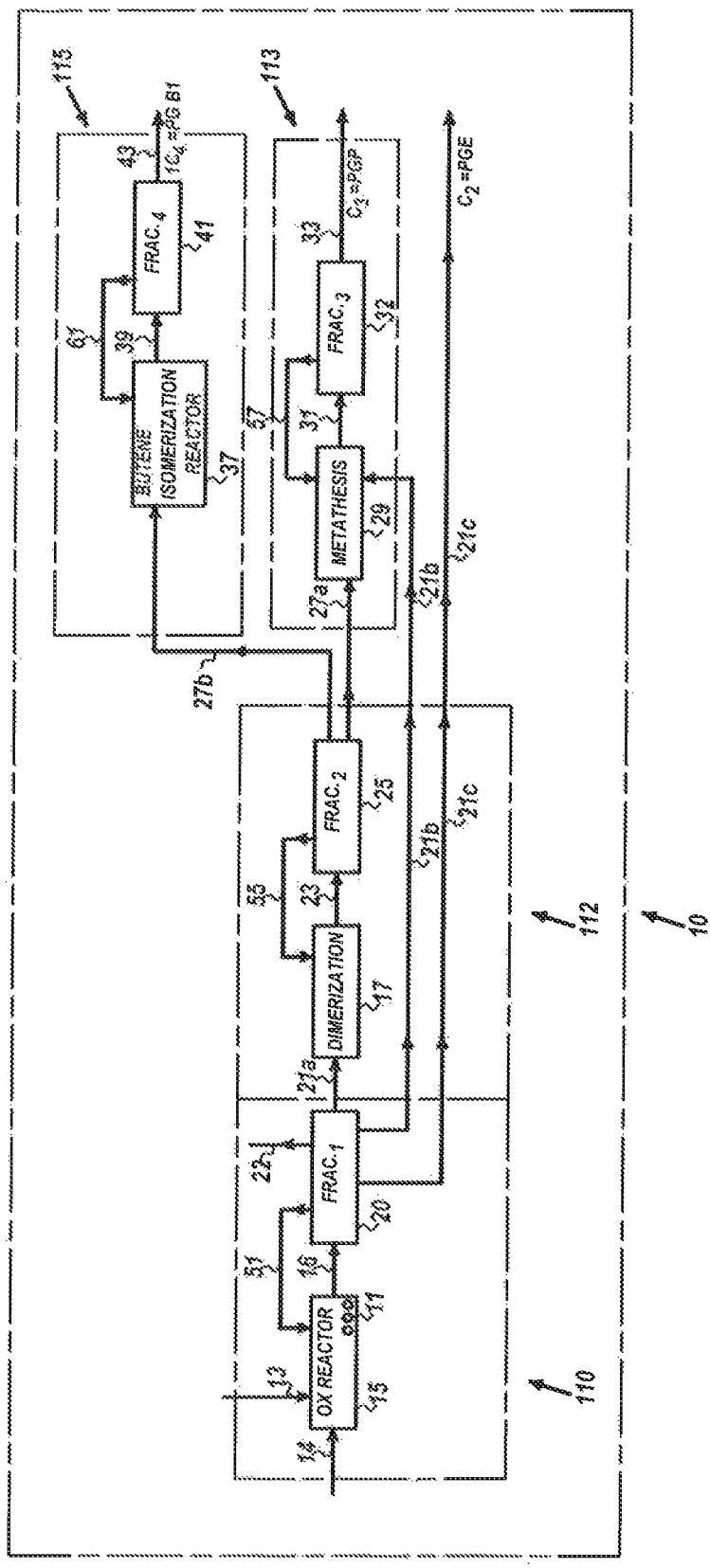
FIG. 2 depicts an oxidative-coupling of methane (OCM) plant according to one or more embodiments.

FIG. 2 depicts an oxidative-coupling of methane (OCM) plant according to one or more embodiments.

The process of converting alkanes 14 to olefin monomers ethylene, propylene, and butene or combinations thereof can use renewable electric power in an oxidative-coupling of methane (OCM) plant 10 while additionally recycling a stream of unconverted methane (C1) 51 from the first fractionation train to the oxidation reactor 15.

The process of converting alkanes 14 to olefin monomers ethylene, propylene, and butene or combinations thereof, can use renewable electric power in an oxidative-coupling of methane (OCM) plant 10 while additionally recycling a stream of unconverted ethylene 55 from second fractionation train 25 to dimerization unit 17.

The process of converting alkanes 14 to olefin monomers ethylene, propylene, and butene or combinations thereof can use renewable electric power in an oxidative-coupling of methane (OCM) plant 10 while additionally recycling a stream of unconverted ethylene and butene 57 from third fractionation train 32 to metathesis reactor 29.

The process of converting alkanes 14 to olefin monomers ethylene, propylene, and butene or combinations thereof, can use renewable electric power in an oxidative-coupling of methane (OCM) plant 10 while additionally recycling a stream of unconverted 2-butene 61 from the fourth fractionation train 41 to the butene isomerization unit 37.

In embodiments, an ethylene plant 110 to make ethylene can include the steps of:

contacting a catalyst 11 in an oxidative reactor 15 with oxygen 13 and a natural gas mixture of alkanes 14 producing a mixture of monomers 16 wherein the catalyst is a member of the group consisting of: a lanthanide series metal supported catalyst and an actinide series metal supported catalyst. The reaction proceeds at a pressure from 6 bar to 16 bar and a temperature of 600 to 800 degrees Celsius; and then the effluent 16 from the oxidation reactor is fractionated in a first fractionation train 20 forming a first, second, and third polymerization grade ethylene streams 21a, 21b and 21c and a carbon dioxide stream 22.

In embodiments, the 2-butene plant 112 to convert ethylene to 2-butene can include the steps of: dimerizing in a dimerization unit 17 the first polymerization grade ethylene stream 21a to form a stream of butene and by products 23 and fractioning the stream of butene and by products 23 in a second fractionation train 25 forming two 2-butene streams 27a and 27b.

In embodiments, the propylene plant 113, to convert the 2-butene and some of the ethylene to form propylene can include the steps of reacting the 2-butene stream 27a in a metathesis reactor 29 with the second polymerization grade ethylene stream 21b from the first fractioning train forming propylene with unconverted ethylene and 1-butene 31 and fractionating the propylene with unconverted ethylene and 1-butene 31 in a third fractionation train 32 forming polymerization grade propylene 33.

The 1-butene plant 115 to isomerize the second 2-butene stream into 1-butene, can include the steps of: isomerizing the second 2-butene stream 27b in a butene isomerization reactor 37 converting 2-butene to crude 1-butene 39 and fractionating crude 1-butene 39 in a fourth fractionation train 41 to produce polymerization grade 1-butene 43.

In embodiments, the process can include the step of using oxygen enhanced combustion in the hydrocarbon fueled heaters and boilers of the APAO plant to limit nitrogen based gas volumes.

The substantially zero carbon emission process for making amorphous poly alpha olefins can be used to make olefin derivatives.

In embodiments, the produced olefin derivative can be a poly olefin wax.

In embodiments, the produced olefin derivative can be propylene glycol.

In embodiments, the produced olefin derivative can be acrylic acid.

In embodiments, the produced olefin derivative can be a poly acrylic acid.

In embodiments, the produced olefin derivative can be a polyethylene.

In embodiments, the substantially zero emission process for making amorphous poly alpha olefins can include employing solar heating instead of renewable electric power for process heat supply.

In embodiments, a distillation column is used to fractionate various mixtures of propylene and propane to produce a composition of greater than 92% propylene with less than 8% propane.

Example 1

A substantially zero carbon emission process for making amorphous poly alpha olefins such as a copolymer of propylene and 1-butene includes converting alkanes of natural gas containing methane, ethane, and nitrogen to olefin monomers of ethane, ethylene, or combinations thereof using renewable electric power.

In this example, the conversion occurs in an oxidative-coupling of methane (OCM) plant using a combination of wind, and solar power, in a ratio of 80:20 wind to solar power.

As a first step, an ethylene plant is used to make ethylene from the natural gas mixture of methane, ethane, and nitrogen.

In this example the natural gas stream has 3% nitrogen, 3% ethane, and the balance of the stream methane. The natural gas stream is reacted with oxygen.

The ethylene can be produced at a rate of 285 kilogram-moles per hour in the OCM plant.

As a second step, a 2-butene plant is used to convert the ethylene to create two 2-butene streams at a total rate of 95 kilogram-moles per hour using a fluidly connected dimerization unit and a fractionation train.

As a third step, a propylene plant is used to convert the first 2-butene stream and some of the ethylene to form propylene using a metathesis unit and another fractionation train. The conversion can be performed at a rate of 118 kilogram-moles per hour.

As a fourth step a 1-butene plant to isomerize the second 2-butene stream into 1-butene uses an isomerization reactor and a fractionation unit. The conversion rate can be performed at a rate of 36 kilogram-moles per hour.

As a fifth step, any one of the created 1-butene, propylene or ethylene, are polymerized in an APAO plant.

Simultaneously, a temperature of 130 degrees to 135 degrees Fahrenheit is used to polymerize the 1-butene, propylene or ethylene from the olefins plant using a residence time of 1 to 2 hours.

Renewable electric power usable with this plant's heaters would be the same mix of solar and wind power.

A solvent, such as mono-ethanol amine, can be used to scrub at least one boiler stack gasses to sequester carbon dioxide from the boiler stack gas.

The resulting APAO is an excellent adhesive. REXtac™ 2730 has typical characteristics used by this process which is incorporated by reference.

The two step process results in substantially zero carbon emissions into atmosphere to create monomers that can be polymerized into amorphous poly alpha olefins.

Example 2

A substantially zero emission process for making amorphous poly alpha olefins such as copolymer of ethylene and propylene includes converting alkanes of natural gas containing methane, ethane, and nitrogen to olefin monomers ethylene, propylene, and 1-butene or combinations thereof using renewable electric power.

In this example, the conversion occurs in an oxidative-coupling of methane (OCM) plant using a combination of wind, and solar power, in a ratio of 50:50 wind to solar power.

As a first step, an ethylene plant is used to make ethylene from the natural gas mixture of methane, ethane and nitrogen.

In this example the natural gas stream has 2% nitrogen, 2% ethane, and the balance of the stream methane. The natural gas stream is reacted with oxygen, which is pure oxygen from an air separation unit.

The ethylene can be produced at a rate of 255 kilogram-moles per hour in the OCM plant.

As a second step, a 2-butene plant is used to convert the ethylene to create two 2-butene streams at a rate of 90 kilogram-moles per hour using a fluidly connected dimerization unit and a fractionation train.

As a third step, a propylene plant is used to convert the first 2-butene stream and some of the ethylene to form propylene using a metathesis unit and another fractionation train. The conversion can be performed at a rate of 100 kilogram-moles per hour.

As a fourth step, a 1-butene plant is used to isomerize the second 2-butene stream into 1-butene using an isomerization reactor and a fractionation unit. The conversion can be performed at a rate of 30 kilogram moles per hour.

As a fifth step, any one of the created 1-butene, propylene or ethylene are polymerized in an APAO plant.

Simultaneously, a temperature of 140 to 150 degrees Fahrenheit is used to polymerize the ethylene and propylene from the olefins plant using a residence time of 1.5 hours.

Renewable electric power usable with this plant's heaters would be the same mix of solar and wind power.

A solvent, such as methyl diethanol amine (MDEA), can be used to scrub at least one boiler stack gas to sequester carbon dioxide from the boiler stack gas. The resulting APAO is an excellent adhesive. REXtac™ RT 2535 has typical characteristics used by this process which is incorporated by reference.

The two step process results in substantially zero carbon emissions into the atmosphere.

Example 3

A substantially zero emission process for making amorphous poly alpha olefins such as terpolymer of 1-hexene, propylene and 1-butene includes converting alkanes of natural gas containing methane, ethane, and nitrogen to olefin monomers ethylene, propylene, 1-butene or combinations thereof using renewable electric power.

In this example, the conversion occurs in an oxidative-coupling of methane (OCM) plant using a combination of wind, and solar power, in a ratio of 100% wind power.

As a first step, an ethylene plant is used to make ethylene from the natural gas mixture of methane, ethane and nitrogen.

In this example the natural gas stream has 2.5% nitrogen, 2.5% ethane, and the balance of the stream methane. The natural gas stream is reacted with oxygen.

The ethylene can be produced at a rate of 275 kilogram-moles per hour in the OCM plant.

As a second step, a 2-butene plant is used to convert the ethylene to create two 2-butene streams at a rate of 100 kilogram-moles per minute using a fluidly connected dimerization unit and a fractionation train.

As a third step, a propylene plant is used to convert the first 2-butene stream and some of the ethylene to form propylene using a metathesis unit and another fractionation train. The conversion can be performed at a rate of 125 kilogram-moles per hour.

As a fourth step a 1-butene plant to isomerize the second 2-butene stream into 1-butene using an isomerization reactor and a fractionation unit. The conversion can be performed at a rate of 40 kilogram-moles per hour.

As a fifth step, any one of the created 1-butene, propylene or ethylene are polymerized in an APAO plant.

Simultaneously, a temperature of 135 degrees to 145 degrees Fahrenheit is used to polymerize the 1-butene, propylene or ethylene from the olefins plant using a reaction residence time of 1.75 hours.

Renewable electric power usable with this plant's heaters would be the same mix of solar and wind power.

A solvent, such as mono-ethanol amine, can be used to scrub at least one boiler stack gasses to sequester carbon dioxide from the boiler stack gas The resulting APAO is sticky. Rolling Ball Tack for this polymer can be 8 to 12 centimeters.

The two step process results in substantially zero carbon emissions into atmosphere to create amorphous poly alpha olefin.

While these embodiments have been described with emphasis on the embodiments, it should be understood that within the scope of the appended claims, the embodiments might be practiced other than as specifically described herein.

What is claimed is:

1. An amorphous poly alpha olefin (APAO) made with substantially zero $CO_2$ emissions made by the process comprising the steps of:
   a. converting alkanes to ethylene, propylene, and 1-butene using renewable electric power in an oxidative-coupling of methane (OCM) plant comprising an ethylene plant, a 2-butene plant, a propylene plant, and a 1-butene plant, by the steps comprising:
      (i) providing an ethylene plant comprising an oxidation reactor and a first fractionation train and converting a natural gas and oxygen in the oxidation reactor to produce an oxidation reactor effluent comprising ethylene and passing the oxidation reactor effluent to the first fractionation train to recover a first ethylene stream, a second ethylene stream, and a third ethylene stream;
      (ii) providing a 2-butene plant comprising a dimerization unit and a second fractionation train and converting a portion of the first ethylene stream in the dimerization unit to produce a dimerization unit effluent comprising 2-butene and passing the dimerization unit effluent to the second fractionation train to recover a first 2-butene stream and a second 2-butene stream;
      (iii) providing a propylene plant comprising a metathesis reactor and a third fractionation train and converting a portion of the first 2-butene stream and a portion of the second ethylene stream in the metathesis reactor to produce a metathesis reactor effluent comprising propylene and passing the metathesis reactor effluent to the third fractionation train to recover the propylene;
      (iv) providing a 1-butene plant comprising a butene isomerization unit and a fourth fractionation train and converting a portion of the second 2-butene stream in the butene isomerization unit to produce a butene isomerization unit effluent comprising 1-butene and passing the butene isomerization unit effluent to the fourth fractionation train to recover the 1-butene;
   b. polymerizing any one of the 1-butene, propylene, or third ethylene stream in an APAO plant comprising boilers in which boiler stack gasses are produced, the polymerization comprising the simultaneous steps of:
      (i) applying a temperature of 130-175° F. to the 1-butene, the propylene or the third ethylene stream from the 1-butene plant, the propylene plant, or the ethylene plant, respectively;
      (ii) using renewable electric power to power the boilers while scrubbing at least one of the boiler stack gasses with a solvent to sequester carbon dioxide from the at least one of the boiler stack gasses;
   wherein the completion of steps (a.) and (b.) results in substantially zero CO2 emissions into the atmosphere and the formation of an amorphous poly alpha olefin.

2. The product made by the process of claim 1, wherein the natural gas comprises methane and the oxidation reactor effluent comprises unconverted methane, and further comprising recycling a stream of the unconverted methane from the first fractionation train to the oxidation reactor.

3. The product made by the process of claim 2, wherein the dimerization unit effluent comprises unconverted ethylene, and further comprising recycling a stream of unconverted ethylene from the second fractionation train to the dimerization unit.

4. The product made by the process of claim 3, wherein the metathesis reactor effluent comprises unconverted ethylene and unconverted 2-butene, and further comprising recycling a stream of unconverted ethylene and unconverted 2-butene from the third fractionation train to the metathesis reactor.

5. The product made by the process of claim 4, wherein the butene isomerization unit effluent comprises unconverted 2-butene, and further comprising recycling a stream of unconverted 2-butene from the fourth fractionation train to the butene isomerization unit.

6. The process of claim 1, wherein converting the natural gas and oxygen in the oxidation reactor to produce the oxidation reactor effluent comprising ethylene comprises:
   a. contacting a catalyst in the oxidation reactor with oxygen and the natural gas at a pressure from 6 bar to 16 bar and a temperature of 600 to 800° C. to produce the oxidation reactor effluent, wherein:
      (i) the catalyst is selected from the group consisting of a lanthanide series metal supported catalyst and an actinide series metal supported catalyst;
      (ii) the natural gas comprises a mixture of alkanes; and
      (iii) the oxidation reactor effluent comprises: ethylene and carbon dioxide.

7. The product made by the process of claim 6, wherein the dimerization unit effluent comprises 2-butene and by-products.

8. The product made by the process of claim 7, wherein the metathesis reactor effluent comprises propylene, unconverted ethylene, and unconverted 2-butene and wherein passing the metathesis reactor effluent to the third fractionation train to recover the propylene further comprises recovering the unconverted ethylene and unconverted 2-butene along with the propylene.

* * * * *